United States Patent
Brombin

(10) Patent No.: US 7,603,829 B2
(45) Date of Patent: Oct. 20, 2009

(54) METHOD AND APPARATUS FOR STERILIZING CONTAINERS OF PLASTIC MATERIAL AND FOR FILLING THEM WITH LIQUID SUBSTANCES

(75) Inventor: Tiziano Brombin, S. Maria Maddalena (IT)

(73) Assignee: I.M.A. Industria Macchine Automatiche, Ozzano Emilia (Bologna) (IT)

( * ) Notice: Subject to any disclaimer, the term of this patent is extended or adjusted under 35 U.S.C. 154(b) by 156 days.

(21) Appl. No.: 10/593,505

(22) PCT Filed: Mar. 31, 2005

(86) PCT No.: PCT/IB2005/000834
§ 371 (c)(1),
(2), (4) Date: Sep. 20, 2006

(87) PCT Pub. No.: WO2005/094905
PCT Pub. Date: Oct. 13, 2005

(65) Prior Publication Data
US 2007/0212255 A1    Sep. 13, 2007

(30) Foreign Application Priority Data
Mar. 31, 2004    (EP)    ................................... 04425229

(51) Int. Cl.
*B65B 55/04*    (2006.01)
*B65B 5/00*    (2006.01)
(52) U.S. Cl. .............................. 53/426; 53/431; 53/317
(58) Field of Classification Search ................. 53/253, 53/331.5, 317, 319, 428, 431, 422, 426
See application file for complete search history.

(56) References Cited

U.S. PATENT DOCUMENTS

| | | | |
|---|---|---|---|
| 3,172,434 A | 3/1965 | Boucher | |
| 4,408,436 A * | 10/1983 | Glover | ........................ 53/247 |
| 4,784,169 A * | 11/1988 | Striedieck | .................... 134/111 |
| 5,713,403 A * | 2/1998 | Clusserath et al. | .......... 141/101 |
| 6,185,910 B1 * | 2/2001 | Achhammer | ................. 53/426 |
| 6,715,266 B2 * | 4/2004 | Browning | .................... 53/492 |

FOREIGN PATENT DOCUMENTS

| | | |
|---|---|---|
| DE | 37 01 915 A1 | 8/1988 |
| DE | 44 16 065 A1 | 10/1995 |
| DE | 199 09 826 A1 | 9/2000 |
| DE | 100 45 585 A1 | 3/2002 |
| FR | 76 31331 | 10/1976 |

* cited by examiner

*Primary Examiner*—Rinaldi I. Rada
*Assistant Examiner*—John Paradiso
(74) *Attorney, Agent, or Firm*—William J. Sapone; Coleman Sudol Sapone P.C.

(57) ABSTRACT

According to method for sterilizing containers (2) of plastic material and for filling the containers with liquid substances, containers (2) are moved in succession along a feeding path (P), so as to enter a a covering structure (S) containing a one-block apparatus for sterilizing and filling and defining a closed aseptic environment. The containers (2) are sterilized in a first portion (6) of the apparatus (1), situated along a first section (T) of the path (P), then weighted filled with a liquid substance and subsequently closed with pre-sterilized plugs/caps, in a second portion (12) of the apparatus (1), situated along a second section (TR) of the path (P), after the first section (T).

9 Claims, 4 Drawing Sheets

METHOD AND APPARATUS FOR STERILIZING CONTAINERS OF PLASTIC MATERIAL AND FOR FILLING THEM WITH LIQUID SUBSTANCES

FIELD OF THE INVENTION

The present invention relates to a method and apparatus for sterilizing containers of plastic material and for filling them with liquid substances.

In particular, the method proposed by the present invention is advantageously used for sterilizing containers or bottles of plastic material, preferably of the LDPE—Low Density Polyethylene type, which are later filled, in an aseptic environment, with liquid substances, preferably foodstuff or similar, thus always closed in aseptic environment.

SUMMARY OF THE INVENTION

The following description will make explicit reference to the foodstuff, without losing generality.

According to a first aspect of the invention, a method for sterilizing containers of plastic material and for filling the containers with liquid substances, includes: feeding said containers in a succession along a feeding path, so as to bring the containers into a covering structure defining a closed aseptic environment containing a one-block apparatus for sterilizing and filling the containers;

sterilizing said containers in a first portion of said apparatus, situated along a first section of said path; weighted filling of said containers with said liquid substance and subsequently closing the filled and weighed containers with pre-sterilized plugs/caps, in a second portion of said apparatus, situated along a second section of said path, after said first section.

According to a second aspect of the invention, a one-block apparatus is claimed for sterilizing and filling containers of plastic material with liquid substances, characterized in that it includes:

a unit for sterilizing and drying the inside of the containers;
a unit for weighted filling said containers with said liquid substance; and
a unit for closing said containers with closing plugs/caps;
said one-block apparatus being contained in a covering structure for defining an aseptic environment;
said sterilizing unit and filling unit being separated by a wall of the covering structure; and
said filling unit being subjected to a circulation or laminar flow of filtered/purified air (LAF—Laminar Flow).

BRIEF DESCRIPTION OF THE DRAWINGS

The present invention will be described in the following, with reference to a preferred, but not exclusive embodiment of a one-block apparatus for filling containers with liquid substances and for closing them in aseptic environment, which apparatus carries out a method in which.

BEST MODES OF CARRYING OUT THE INVENTION

Figure 1:
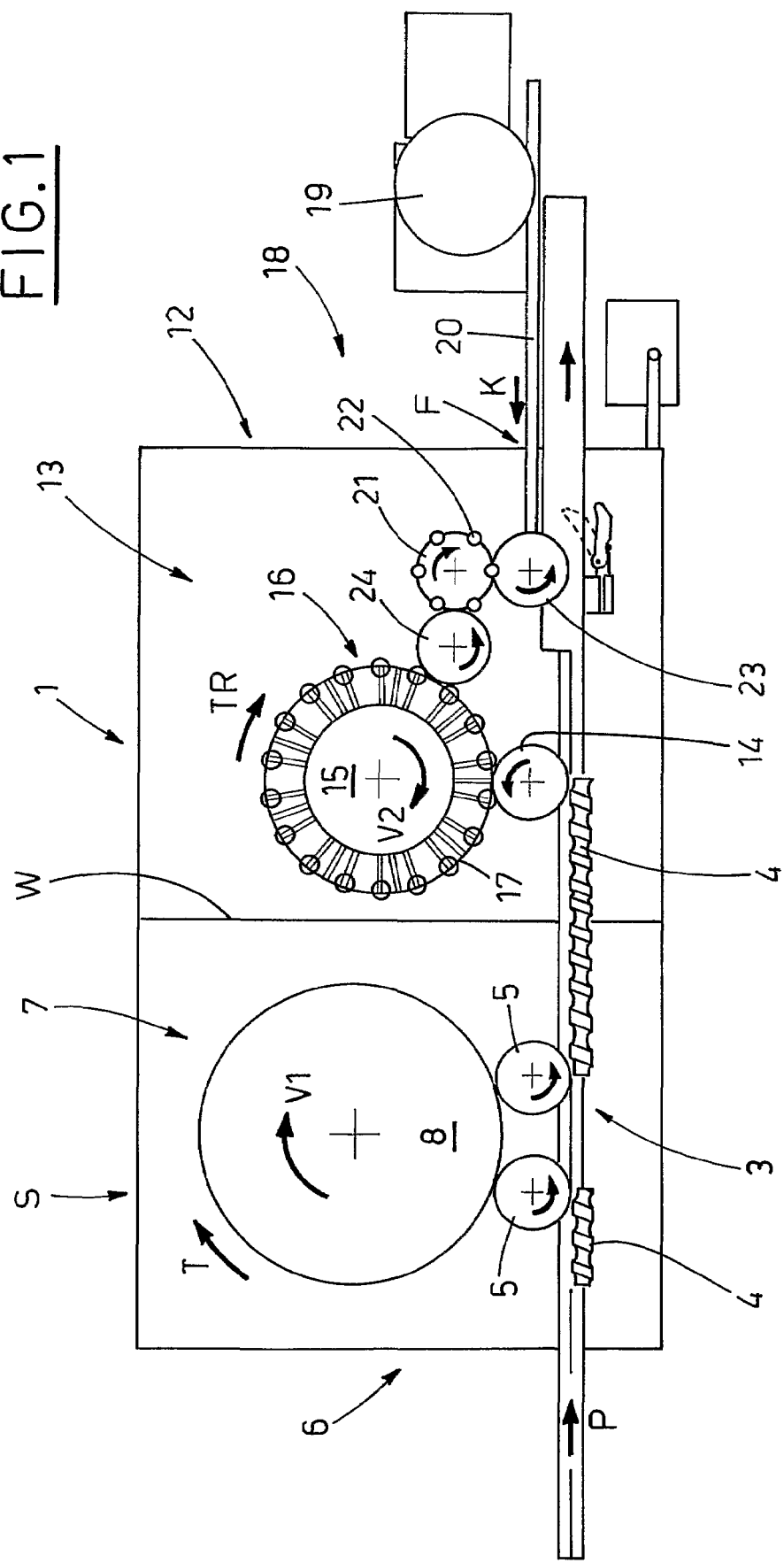
FIG. 1 is a schematic, partially sectional top view and with some parts removed for sake of clarity, of a one-block apparatus for filling containers with liquid substances and closing them in an aseptic environment, which apparatus carries out the method proposed by the present invention.
Figure 2:
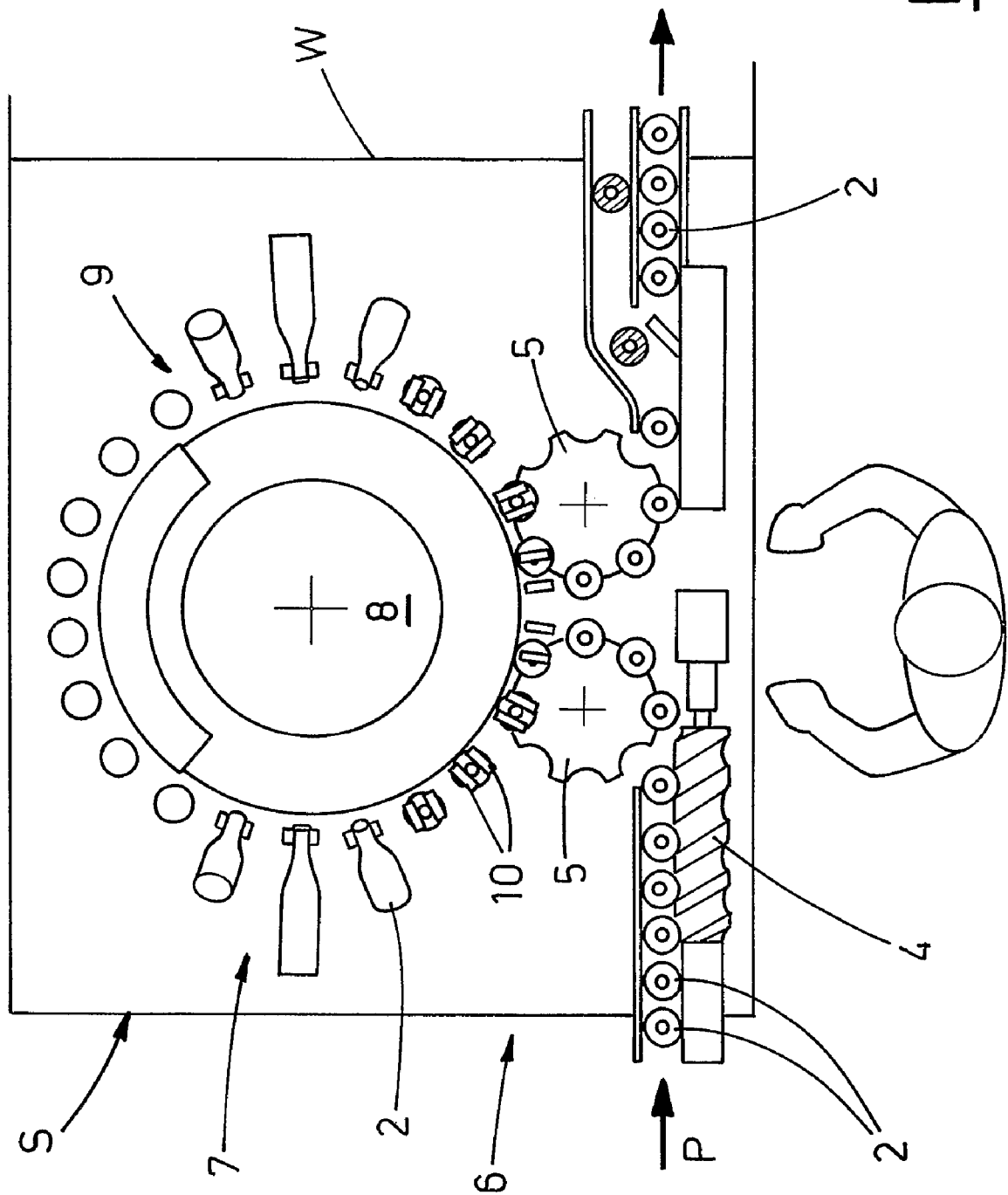
FIG. 2 is a schematic top view of a portion of the apparatus of FIG. 1.
Figure 3:
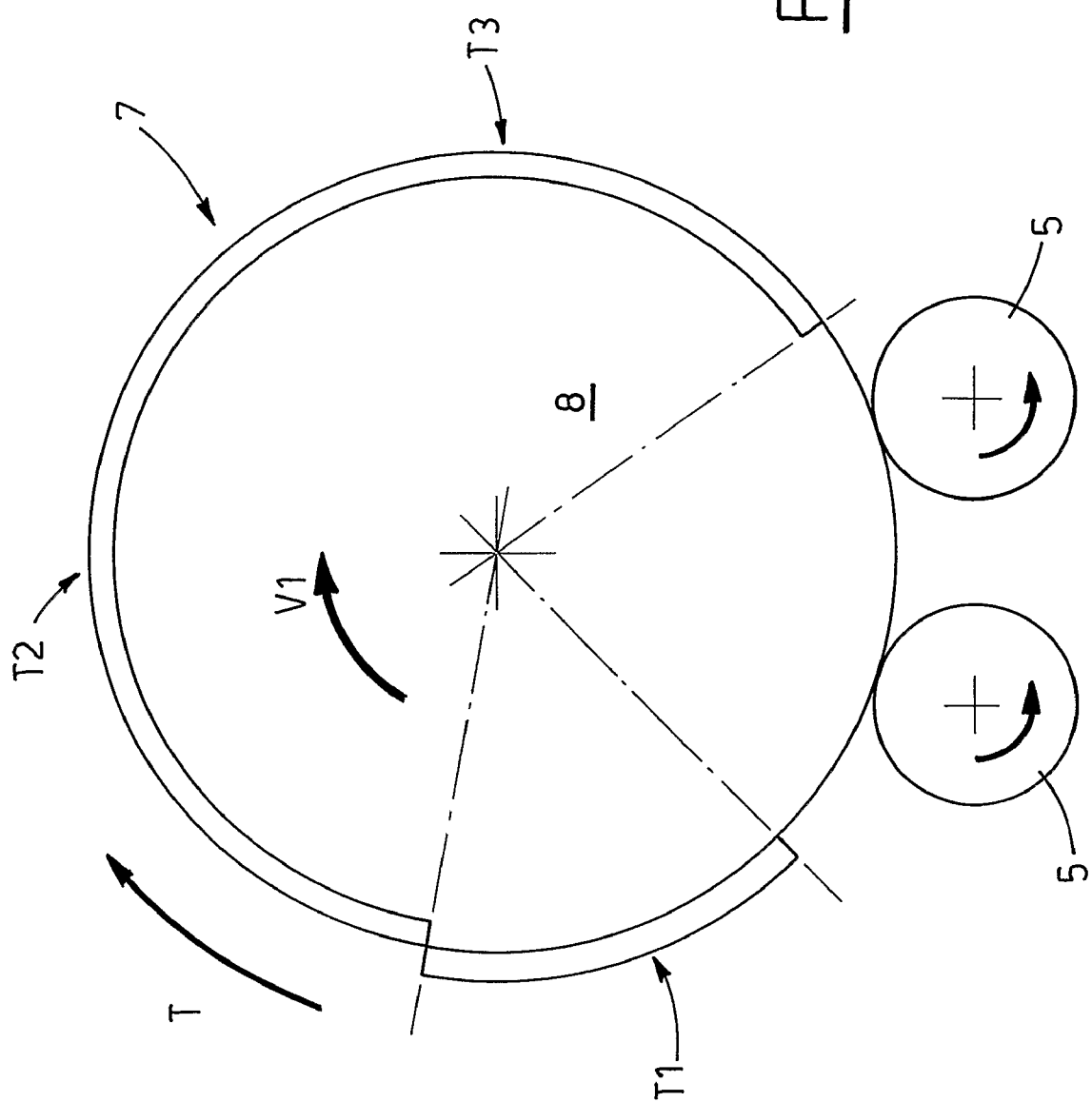
FIG. 3 is a schematic view of a portion of FIG. 2 with some parts corresponding to relevant steps of the proposed method highlighted.

With reference to the enclosed FIGS. 1, 2 and 3, the reference numeral 1 indicates a one-block apparatus for filling containers 2 with liquid substances.

In particular, the apparatus 1 is entirely enclosed within a containing structure S, inside which an aseptic environment is formed.

In particular, the containers 2 are bottles of plastic material, preferably the LDPE—Low Density Polyethylene, which are fed to the apparatus 1 along a feeding path P, by means of a continuous conveyor 3, a pair of Archimedean screws 4 and star conveyors 5, in order to be filled with liquid substances, preferably liquids used in foodstuff processing field and similar.

According to FIGS. 1 and 2, the one-block apparatus 1 is defined by a first portion 6 including a unit 7 for sterilizing and drying the containers 2.

The unit 7 includes a turret or rotating carrousel 8 (rotation direction V1) and has a sequence of work stations 9 for processing the containers 2 along a circular section T of the path P, defined by the rotation of the carrousel 8.

According to what has been better shown in FIG. 2 and in FIG. 3, the carrousel 8 is operated by the stations 9 to take the containers 2, one by one, by means of pliers 10. The containers are arranged vertically, aligned and with the openings turned upwards, in a part T1 of the section T, and are moved so as to be overturned gradually about a horizontal axis, until the containers 2 have the openings facing downwards, that is until they are turned by 180° with respect to the initial position, in which the containers 2 are withdrawn by the carrousel 8.

The containers 2 are kept in the overturned position along a part T2 of the section T, and finally, along the part T3 of the section T, they are gradually brought back to the initial position, with the openings turned upwards, again overturned by 180° with respect to the position taken in the part T2, ready to enter the star conveyor 5, the Archimedean screw 4 and then the conveyor 3 again.

The carrousel 8 has nozzles 11 (FIG. 4), supported together with the pliers 10, and moved by cam moving means, known and not shown, carried by the carrousel 8, to enter gradually, through the opening, into each container 2, and to reach a selected position inside the container 2.

Figure 4:
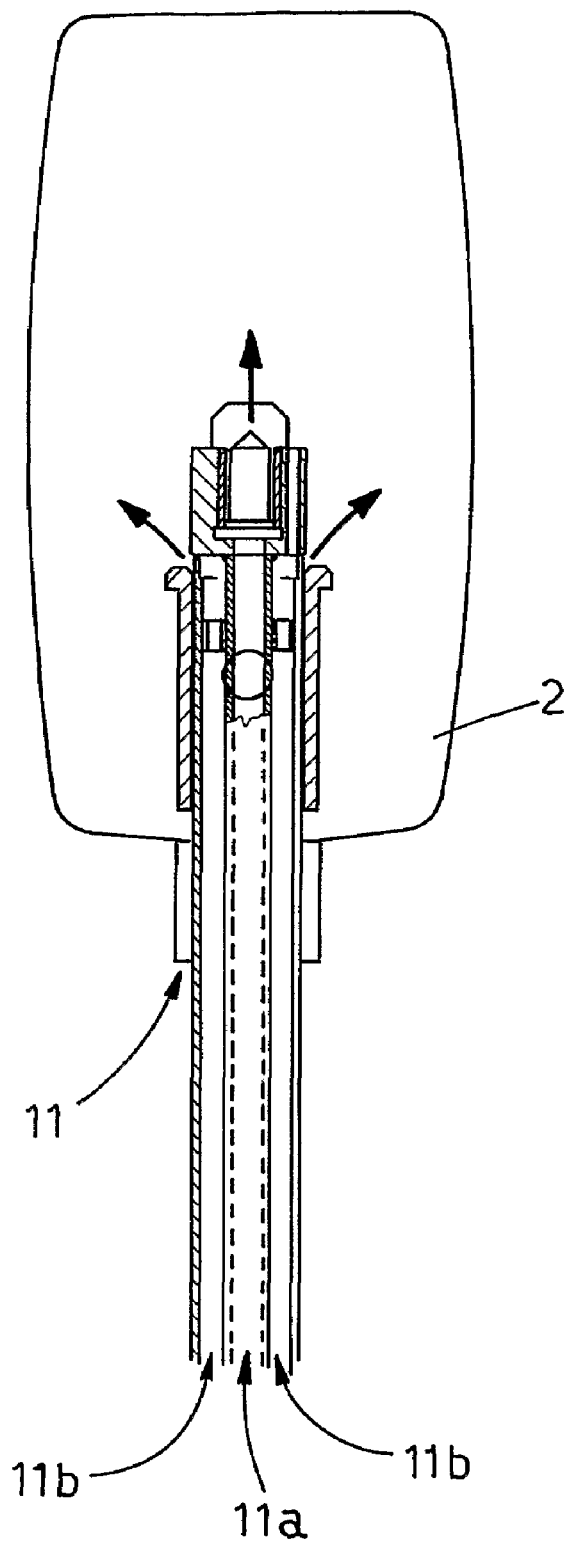
FIG. 4 is a schematic, partially sectional view with some parts removed for sake of clarity, of a working element of the apparatus of FIG. 1.

According to what is better shown in FIG. 4, the nozzles 11 have a triple inner canalization, that is a central canalization 11a and two lateral canalizations 11b, which are connected in a known and not shown way by relative feeding ducts and pumps, to a tank of a sterilizing substance, to a source of steam, and to a source of purified sterile pressurized air, in order to sterilize, steam wash and subsequently dry the inside of the containers 2.

In particular, the sterilizing substance contained in the tank is hydrogen peroxide $H_2O_2$ (preferably, but not exclusively 35% Oxipack S Ecolab, produced and marketed by Henkel).

More in detail, along the part T1, each nozzle 11 introduces into the opening of a relative container 2, entering it gradually, to diffuse, through the central canalization 11a, by atomizing, the hydrogen peroxide $H_2O_2$, so as to sterilize the inner surface of the mouth, as well as, subsequently the whole space defined by the inner walls of the container 2.

When the feeding of the hydrogen peroxide $H_2O_2$ to the nozzle 11 is stopped upon reaching of the part T2, the nozzle 11 is fed through the canalizations 11b with pressurized steam, so as to perform a further sterilizing action inside the container 2 through a steam bath.

Finally, when the part T3 has been reached and the steam feeding is interrupted, the so sterilized inside of the container 2 is subjected to a final drying performed by the nozzle 11 and by the sterile air fed thereto and passing through the canalizations 11b.

The nozzle 11 begins to leave gradually the container 2, while the latter is gradually brought to its initial position with the opening turned upwards.

According to FIG. 1, the apparatus 1 includes also a second portion 12, which is separated from the portion 6 by a wall W, being a part of the structure S and inside which filtered/purified air known as LAF or Laminar Flow, circulates.

The portion 12 includes a unit 13, where the containers 2 coming from the conveyor 3 through the Archimedean screw 4 and a star conveyor 14, are weight filled with the liquid substance.

The unit 13 is a turret or rotating carrousel 15 (rotation direction V2), which has a sequence of work stations 16 for weighted filling and contemporaneously weighing the containers 2 along the circular section TR of the path P defined by the rotation of the carrousel 15.

In particular, each station 16 includes pliers 17, which hold a relative container 2, a nozzle for aseptic filling (known and not shown), which enters the container 2.

The station 16 carries a load cell scale (known and not shown), on which the container 2 is situated to be weighed during the filling operation.

Each load cell is connected to a control unit (not shown), to check the net weight of each container 2 with the liquid substance.

According to FIG. 1, the apparatus 1 includes also a unit 18 for applying screw caps or closing plugs (known and not shown) on each filled and weighed container 2.

The unit 18 includes a hopper 19 of pre-sterilized plugs, a conveyor 20, which feeds the plugs in succession (direction K), by a conveying roll 23, to a turret 21, which plugs by shafts 22.

The turret 21 and the conveying roll 23 are prepared in such a way, as to support the plugs to be fed to a conveying roll 24, which transfers the filled and weighed containers 2 leaving the carrousel 15, so as to arrange the plugs over the containers 2, in order to close them tightly (by screwing), as well as the plugged containers 2, which are fed by the turret 21 and the roll 22 above the conveyor 3, conveying them outside the apparatus 1.

It is to be pointed out that, when they pass through a slot F made in the structure S, the caps or plugs fed by the conveyor 20 in the direction K are subjected to the purifying action of the filtered air under LAF, which circulates inside the portion 12 of the apparatus 1 and which can also flow from the portion 12 to the portion 6 through the holes made in the wall W.

The apparatus 1, so enclosed in the structure S, has another big advantage, resulting from the fact, that it can be subjected to washing/cleaning/sterilizing operations in place, such operations commonly known to the technicians as CIP/SIP—Cleaning in Place/Sterilizing in Place.

The invention claimed is:

1. A method for sterilizing containers (2) made of a plastic material and for filling the containers with liquid substances comprising the steps of:

feeding said containers (2) in a succession along a feeding path (P), so as to bring the containers (2) into a covering structure (S) defining a closed aseptic environment containing a one-block apparatus for sterilizing and filling the containers;

sterilizing said containers (2) in a first portion (6) of said one-block apparatus (1), situated along a first section (T) of said path (P), said sterilizing step including:

providing a plurality of work stations (9), each of said work stations (9) including plier means (10) for holding and overturning the containers (2) and for bringing each container from a position with an opening turned upwards to a position in which the opening is turned downwards, and vice-versa, nozzle means (11) connected to said plier means (10);

using said plier means to hold and overturn each container for positioning the container so that the opening is turned downwards, the nozzle means entering said opening of said container (2);

discharging a fluid through the nozzle means inside of the container, to sterilize an inside of said container while the container is held and transported by said plier means, thereby diffusing a sterilized substance inside each container (2) fed along a first part (T1) of said first section (T);

diffusing pressurized steam inside each container (2), while moving the container along a second part (T2) of said first section (T) located after said first part (T1); and drying the inside of the container (2) by feeding filtered sterile air through an opening of the container while moving the container forward along a third part (T3) of said section (T);

weighed filling of said sterilized containers (2) with said liquid substance; and, subsequently closing each filled and weighed container with a pre-sterilized plug/cap, in a second portion (12) of said one-block apparatus (1), situated along a second section (TR) of said path (P), located after the first section (T).

2. The method as claimed in claim 1 wherein said sterilizing substance is hydrogen peroxide.

3. The method as claimed in claim 1 wherein said covering structure (S) has a wall (W) separating said second portion (12) from said first portion (6), and further comprising circulating a laminar flow of filtered/purified air inside said second portion (12).

4. The method as claimed in 1 wherein said containers (2) are made of low density polyethylene.

5. The method as claimed in claim 1 wherein said filling substance is a liquid substance used in food.

6. A one-block apparatus (1) for sterilizing and filling containers (2) made of a plastic material with liquid substances, the one-block apparatus comprising:

a unit (7) for sterilizing and drying an the inside of each container (2);

a unit (13) for weighted filling of each container (2) with said liquid substances; and a unit (18) for closing each filled container (2) with a closing plug/cap;

said one-block apparatus being contained in a covering structure (S) for defining an aseptic environment;

said sterilizing unit (7) and said weighed filling unit (13) being separated by a wall (W) of the covering structure (S);

means for subjecting said filling unit (13) to a circulation or laminar flow of filtered/purified air;

said sterilizing unit (7) including:

a rotating turret (8) having a plurality of work stations (9), each of said work stations (9) including plier means (10)

for holding and overturning the containers (2) and for bringing each container from a position with an opening turned upwards to a position in which the opening is turned downwards, and vice-versa; and, nozzle means (11) connected to said plier means (10), the nozzle means entering said opening of said containers (2) to discharge a fluid inside of the containers, to sterilize an inside of said container while the container is held and transported by said plier means.

7. An apparatus as claimed in claim 6 wherein said nozzle means (11) have a triple inner canalization (11a, 11b), a first canalization of each of said nozzle means (11) being connected to a tank of a sterilizing substance to diffuse said sterilizing substance inside said containers (2), second and third canalizations (11b) of each of said nozzle means (11) being connected alternately with a source of pressurized steam and with a source of purified sterile air, to wash and dry the inside of said containers (2) before said containers are filled.

8. An apparatus as claimed in claim 6 wherein said containers (2) are made of low density polyethylene.

9. An apparatus as claimed in claim 6 wherein said filling unit (13) fills the containers (2) with a liquid substance used in food processing.

* * * * *